US006318370B1

(12) United States Patent
Sempere et al.

(10) Patent No.: US 6,318,370 B1
(45) Date of Patent: Nov. 20, 2001

(54) LIP PROTECTOR

(75) Inventors: Juan Jose Albert Sempere, Real, 4, Albaida, Valencia; Loreno Perez Calderon, Valencia, both of (ES)

(73) Assignee: Juan Jose Albert Sempere, Valencia (ES)

( * ) Notice: Subject to any disclaimer, the term of this patent is extended or adjusted under 35 U.S.C. 154(b) by 0 days.

(21) Appl. No.: 09/421,946

(22) Filed: Oct. 21, 1999

(30) Foreign Application Priority Data

Oct. 21, 1998 (ES) ............................................... U9802645

(51) Int. Cl.[7] ....................................................... A61F 11/00

(52) U.S. Cl. ............................ 128/857; 128/859; 84/453

(58) Field of Search .................................... 128/845, 846, 128/857, 858, 859; 433/91, 93, 94, 136, 137; 84/453

(56) References Cited

U.S. PATENT DOCUMENTS

| | | | |
|---|---|---|---|
| 4,338,928 * | 7/1982 | Martin | 128/857 |
| 5,152,300 * | 10/1992 | Horst | 128/857 |
| 5,462,067 * | 10/1995 | Shapiro | 128/859 |
| 5,717,993 * | 2/1998 | Roberts | 128/857 |

* cited by examiner

*Primary Examiner*—Michael A. Brown
(74) *Attorney, Agent, or Firm*—Breiner & Breiner, L.L.C.

(57) ABSTRACT

The invention consists of a lip protector made in one piece, which has been manufactured from a relatively flexible thermoplastic material and configured as an arched body showing a protective outer surface which includes a portion of peripheral wall at the front and has a channel running under it for its full length.

1 Claim, 1 Drawing Sheet

LIP PROTECTOR

Figure 1:
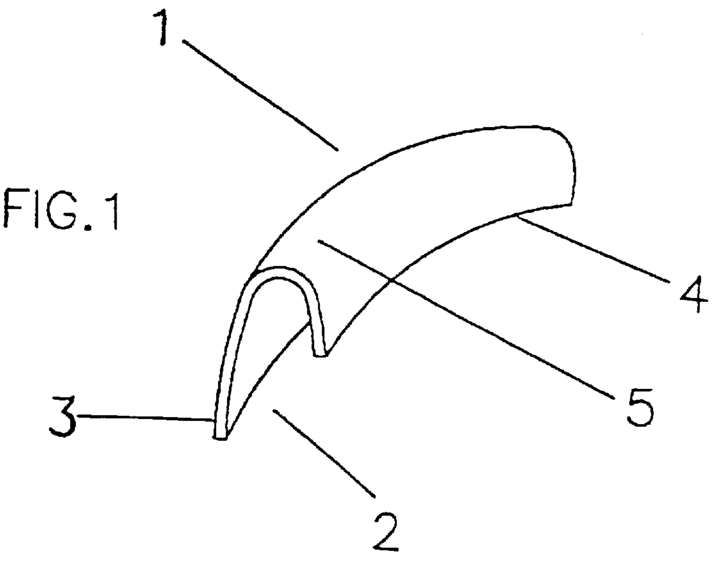

The invention consists of a lip protector made in one piece, which has been manufactured from a relatively flexible thermoplastic material and configured as an arched body showing a protective outer surface which includes a portion of peripheral wall at the front and has a channel running under it for its fill length.

By means of the channel, the lip protector can be fitted to cover the crown of the lower dental arch of its user, for example that of a wind instrument player such as a clarinettist. The outer protective surface prevents direct contact between the dental crown and the fold of the lower lip of the instrumentalist, thus avoiding the erosion of the labial mucous membrane close to the fold which frequently occurs among these instrumentalists, due to the fact that the mouthpiece of the instrument rests on it and rubs against it.

The aim of the invention is to supply the market with a lip protector for wind instrument players or other users, designed in an efficient manner for the purpose of preventing the erosion of the mucous membrane of the lower lip which is habitually caused by the action of the mouthpiece of a wind instrument, for example a clarinet, due to its position against the teeth.

This aim can be achieved by means of the lip protector which is manufactured from a relatively flexible thermoplastic material and configured as an arched body consisting of a peripheral wall for holding and has a channel running under it for its fill length by which the protector is fitted over the lower dental arch of the player who uses it, the crown of which it covers, in order to prevent direct contact between the crown and the fold of his or her lower lip and consequently the eroding of the labial mucous membrane close to the fold which habitually occurs in wind instrument players with the supporting and rubbing of the mouthpiece of the instrument.

Observing the first figure, it can be appreciated that the lip protector is formed by an arched body (1), under the length of which runs a fitting channel (2) with section of inverted "U" shape, one aim of which is a front portion of peripheral holding wall (3) and the other is a rear portion of peripheral holding and supporting wall (4), the two portions of wall being substantially parallel to each other and converging together in an outer protective surface (5).

The simplified section offered in the second figure shows a human mouth (6), in which can be appreciated the lower and upper lips (7 and 8 respectively), and close to them the lower and upper dental arches 9 and 10 respectively).

Close to the mouth (6) can be seen the end portion of a musical wind instrument (11) and its mouthpiece (12) between the lower lips (7) and upper lips (8), resting on the lower one. On the lower dental arch (9), covering its crown, can be seen the arched body (1).

The invention has been described according to the mode of realisation illustrated. It is obviously possible to modify details, for example, with regard to the precision of the arching, extension and degree, as required, or in the configuration, amplitude or extension of the outer protective surface, without going beyond the framework of the invention.

A preferred realisation of the invention suggests that the lip protector should be made by heat moulding of thermoplastic materials, and should be of a relatively flexible nature so as not to cause any damage in use.

In this realisation, the lip protector is an arched body, under the whole length of which runs a channel of inverted "U" shape for fitting the protector to the lower dental arch, bounded on the longer sides by a first portion of peripheral holding wall at the front and a second portion of wall for holding and supporting, at the rear, both walls being substantially parallel to each other, and converging together at the top in an outer protective surface which will keep the upper and lower dental arches separated.

For a better understanding of the above, we attach hereto a descriptive memorandum of a set of drawings showing the object of the invention in one of its preferred realisations, though the said graphic representation should not be construed as constituting any limitation of the peculiar characteristics of this application.

FIG. 1. Shows the lip protector suggested by the invention, by means of a rear view taken from a higher angle. For greater precision, the concealed edges that define its shape are indicated by lines.

Figure 2:
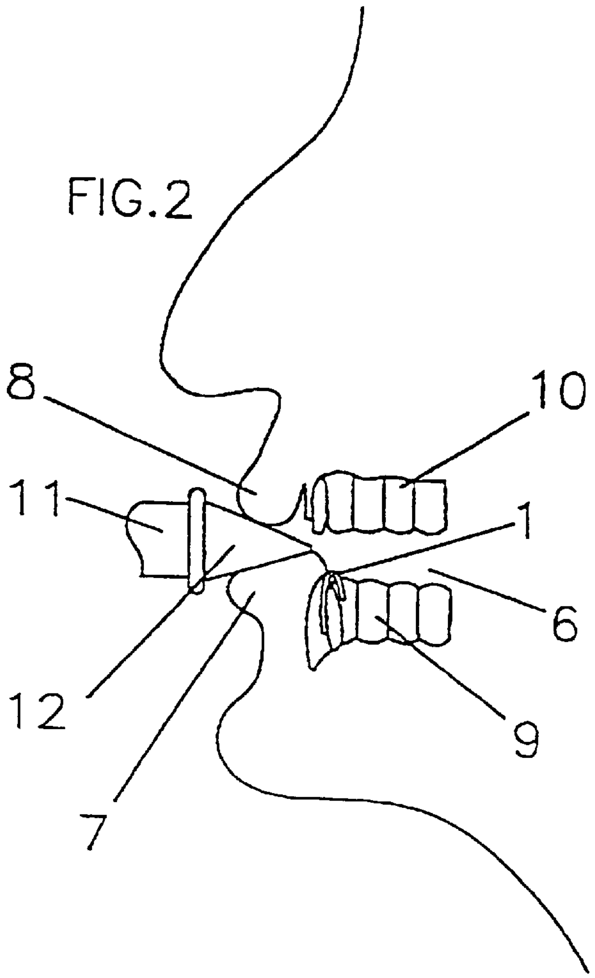

FIG. 2. Illustrates, in a simplified way, the longitudinal section of a human mouth in which can be appreciated the end of a musical instrument with its mouthpiece, and the disposition of the lip protector, as in the invention, on the lower dental arch.

The lip protector can be manufactured at an economical production cost, by the heat moulding of plastic materials, obtaining a rigid section whose shape is substantially similar to that of the letter "U", although the extent of the invention should also be understood to include the obtaining of a lip protector obtained by a thin sheet of material which when used can be bent or folded to configure the desired outer protective surface and the U-shaped channel allowing the lip protector to be fitted over the crown of the lower dental arch and is held there by the support of the peripheral portion of holding wall between the lip and the lower dental arch and, for example, ensuring retention with the collaboration of a second supporting and holding wall at the rear.

It is evident that the lip protector can be made from other materials than thermoplastics, without altering the essential nature of the invention.

It is also evident that the lip protector must present a configuration free of rough surfaces, sharp ridges or corners that may cause erosion or other damage to the surfaces in contact with it.

The lip protector whose registration is sought herein has been designed, both in satisfying the requirements of users as to durability, economy, ergonomics, hygiene, safety, etc., and in the resolution of production plans.

What is claimed is:

1. A lip protector for protection of the lower lip of a wind instrument player from contact with a lower dental arch comprising in combination, a lower dental arch covering body of a thin flexible plastic sheet material having a front peripheral wall for extending downwardly in a position for abutting a frontal region of the lower dental arch, a protective upper crown cap extending from the front peripheral wall defining a "U" shape channel for capping teeth of the lower dental arch and a rear peripheral wall extending from said crown cap downwardly in a position for abutting a rear facing region of the lower dental arch, wherein said front peripheral wall extends downward a further distance than said rear peripheral wall extends downward to thereby retain said lip protector on the lower dental arch and prevent direct contact between the crown of the teeth and the lower lip.

* * * * *